United States Patent
Shcherbakov et al.

(10) Patent No.: US 9,400,254 B2
(45) Date of Patent: Jul. 26, 2016

(54) METHOD AND DEVICE FOR MEASURING CRITICAL DIMENSION OF NANOSTRUCTURE

(71) Applicant: SAMSUNG ELECTRONICS CO., LTD., Suwon-si (KR)

(72) Inventors: Alexander Viacheslavovich Shcherbakov, Moscow region (RU); Maxim Vladimirovich Riabko, Moscow region (RU); Alexey Dmitrievich Lantsov, Moscow region (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/669,536

(22) Filed: Mar. 26, 2015

(65) Prior Publication Data
US 2015/0276378 A1  Oct. 1, 2015

(30) Foreign Application Priority Data

Mar. 26, 2014 (RU) ................................ 2014111735
Dec. 2, 2014 (KR) ......................... 10-2014-0170820

(51) Int. Cl.
*G01N 21/956* (2006.01)
*G01B 11/02* (2006.01)
(Continued)

(52) U.S. Cl.
CPC .............. *G01N 21/956* (2013.01); *G01B 11/02* (2013.01); *G01N 21/93* (2013.01); *G03F 7/70625* (2013.01); *G01B 2210/56* (2013.01); *H01L 22/12* (2013.01); *Y10S 977/88* (2013.01)

(58) Field of Classification Search
None
See application file for complete search history.

(56) References Cited

U.S. PATENT DOCUMENTS 6,181,817 B1 * 1/2001 Zabih ................ G06F 17/30256
382/170
8,881,067 B2 * 11/2014 Nagatomo ......... G06K 9/00798
716/51

(Continued)

FOREIGN PATENT DOCUMENTS

KR  10-2006-0060276 A  6/2006

OTHER PUBLICATIONS

Attota, Ravikiran, et al., "Optical Through-Focus Technique that Differentiates Small Changes in Line Width, Line Height and Sidewall Angle for CD, Overlay, and Defect Metrology Applications," Proc. of SPIE vol. 6922, pp. 69220E-1-69220E-12, (2008).*

*Primary Examiner* — Gordon J Stock, Jr.
(74) *Attorney, Agent, or Firm* — Sughrue Mion, PLLC (57) ABSTRACT

Provided are a method and device for measuring a critical dimension of a nanostructure. The method includes acquiring a reference intensity distribution, in each of a number of spectral bands, of light scattered by at least one reference nanostructure, for each of a number at different positions of the at least one reference nano structure disposed along an optical axis; generating a library of reference intensity distribution arrays based on a number of the reference intensity distributions, determining an intensity distribution of light scattered by a nanostructure under investigation, for each of the number of spectral bands, at each of the number of different positions of the nanostructure under investigation disposed along the optical axis; generating an intensity distribution array by using the determined intensity distributions, and determining information about a critical dimension of the nanostructure under investigation by comparing the intensity distribution array with the library of reference intensity distribution arrays.

15 Claims, 4 Drawing Sheets

(51) Int. Cl.
*G01N 21/93* (2006.01)
*G03F 7/20* (2006.01)
*H01L 21/66* (2006.01)

(56) References Cited

U.S. PATENT DOCUMENTS

| | | |
|---|---|---|
| 2005/0140988 A1 | 6/2005 | Lee et al. |
| 2009/0299681 A1* | 12/2009 | Chen .................. G01N 21/9501 702/123 |
| 2010/0110103 A1* | 5/2010 | Ramirez ................. G06K 9/622 345/619 |
| 2013/0077101 A1* | 3/2013 | Sharoni ................... G03F 1/144 356/625 |
| 2013/0107030 A1 | 5/2013 | Koptyaev et al. |
| 2013/0211760 A1* | 8/2013 | Chu ...................... G01N 21/4788 702/81 |
| 2014/0198322 A1* | 7/2014 | Kim ....................... G01B 11/24 356/625 |
| 2014/0362385 A1* | 12/2014 | Uemura ............. G01B 11/2441 356/511 |

* cited by examiner

METHOD AND DEVICE FOR MEASURING CRITICAL DIMENSION OF NANOSTRUCTURE

RELATED APPLICATIONS

This application claims the benefit of Korean Patent Application No. 10-2014-0170820, filed on Dec. 2, 2014, in the Korean Intellectual Property Office and of Russian Patent Application No. 2014111735, filed on Mar. 26, 2014, the disclosures of which are incorporated herein by reference in their entireties.

BACKGROUND

1. Field

Apparatuses and methods consistent with exemplary embodiments relate The to a method and device for measuring a critical dimension of a nanostructure.

2. Description of the Related Art

Currently-produced semiconductor chips often markedly reduce the critical dimensions of commercial structures. The dimensions of nanostructures that are of interest are approximately several tens of nanometers and are referred to as a "critical dimension". Here, the term "nanostructures" is used to refer to objects that include details on a nanoscale. Currently feasible critical dimensions are about 20 nm, but in the near future this value may be decreased to about 10 nm. There has been a need for accurate and reliable measuring equipment, as well speedy and cost-effective measurement processes, in order to massively produce semiconductor structures with such low critical dimensions.

SUMMARY

One or more exemplary embodiments may provide a method and a device for measuring a critical dimension of a nanostructure by implementing a method of multispectral imaging.

Additional exemplary aspects and advantages will be set forth in part in the description which follows and, in part, will be apparent from the description, or may be learned by practice of the presented exemplary embodiments.

According to an aspect of an exemplary embodiment, a method of multispectral imaging for measuring a critical dimension of a nanostructure may include: acquiring a reference intensity distribution, for each of a plurality of spectral ranges of light scattered by a reference object at each of a plurality of different positions of the reference object disposed along an optical axis; generating a library of reference intensity distribution arrays with a dimension $i*j*m*n$, by using the reference intensity distributions (wherein, i is a horizontal resolution of an image sensor, j is a vertical resolution of the sensor, n is a number of spectral bands used, m is a number of positions of the reference objects along the optical axis); positioning an object under investigation along the optical axis; illuminating the object under investigation with light in a broad frequency spectrum; collecting light scattered by the object under investigation and transmitting the light through a spectral selection unit to the image sensor; determining an intensity distribution of light scattered by the object under investigation with respect to each of a plurality of spectral ranges at each of a plurality of different positions of the object under investigation, by using the image sensor; generating an intensity distribution array with a dimension $i*j*m*n$, by using the determined intensity distribution (wherein i is the horizontal resolution of the image sensor, j is the vertical resolution of the image sensor, n is the number of spectral bands used, m is the number of positions of the object under investigation disposed along the optical axis); and determining information about a critical dimension of the object under investigation by comparing the intensity distribution array with the library of reference intensity distribution arrays.

The light with a broad frequency spectrum may have a wavelength of about 380 nm to about 740 nm.

The reference object may be a calibrated reference object and may have known dimensions.

The generating the library of the reference intensity distribution arrays may include mathematically modeling reference intensity distributions of light scattered by each of a plurality of reference objects with predetermined geometrical parameters.

The mathematically modeling may include using a solution of Maxwell's equations using a numerical method.

The numerical method may include at least one of a rigorous coupled wave analysis (RCWA) and a finite difference time domain (FDTD) method.

The transmitting the light through the spectral selection unit to the image sensor may further include identifying spectral bands from the light collected by the spectrum selection unit.

According to an aspect of another exemplary embodiment, a device for measuring a critical dimension of a nanostructure may include: an optical radiation source emitting light with a broad spectrum; an illuminating optical system illuminating a sample with the light with a broad spectrum; a collecting optical system collecting light scattered by the sample; a spectrum selection unit adjusting a passband of light collected by the collecting optical system; an image sensor receiving an optical signal that passed through the spectrum selection unit; a controller generating an intensity distribution array with a dimension $i*j*m*n$, by using an intensity distribution of the scattered light (wherein i is the horizontal resolution of the image sensor, j is the vertical resolution of the image sensor, n is a number of spectral bands used, m is a number of positions of the object under investigation disposed along the optical axis); and a computing unit for determining a critical dimension of the sample under investigation based on the intensity distribution array.

The sample may include a reference object and an object under investigation, and the computing unit may include a computing unit that determines a critical dimension of the sample under investigation by comparing an intensity distribution array of the reference object and an intensity distribution array of the object under investigation.

The light with a broad spectrum may have a wavelength of about 380 nm to about 740 nm.

The illuminating optical system may include a micro lens, a condenser lens, a polarizer, an amplitude mask, a beam splitter, and a transmitting lens for generating an image of the amplitude mask in the rear focal plane of the micro lens.

The spectrum selection unit may include a set of colored filters disposed in a motor-driven frame, an imaging spectrometer comprising a monochromator and a predetermined optical system, or a charge-coupled device (CCD) or complementary metal-oxide semiconductor (CMOS) array color image sensor.

The image sensor and the spectrum selection unit may be an imaging spectrometer that sequentially records intensity distributions of light scattered by the sample with respect to each spectral band.

The image sensor and the spectrum selection unit may be a color image sensor based on a solid-state charge-coupled device (CCD) or complementary metal-oxide semiconductor (CMOS) array, and the color image sensor concurrently may record intensity distributions of light scattered by the sample with respect to each spectral band.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

DETAILED DESCRIPTION

Reference will now be made in detail to exemplary embodiments which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

Figure 1:
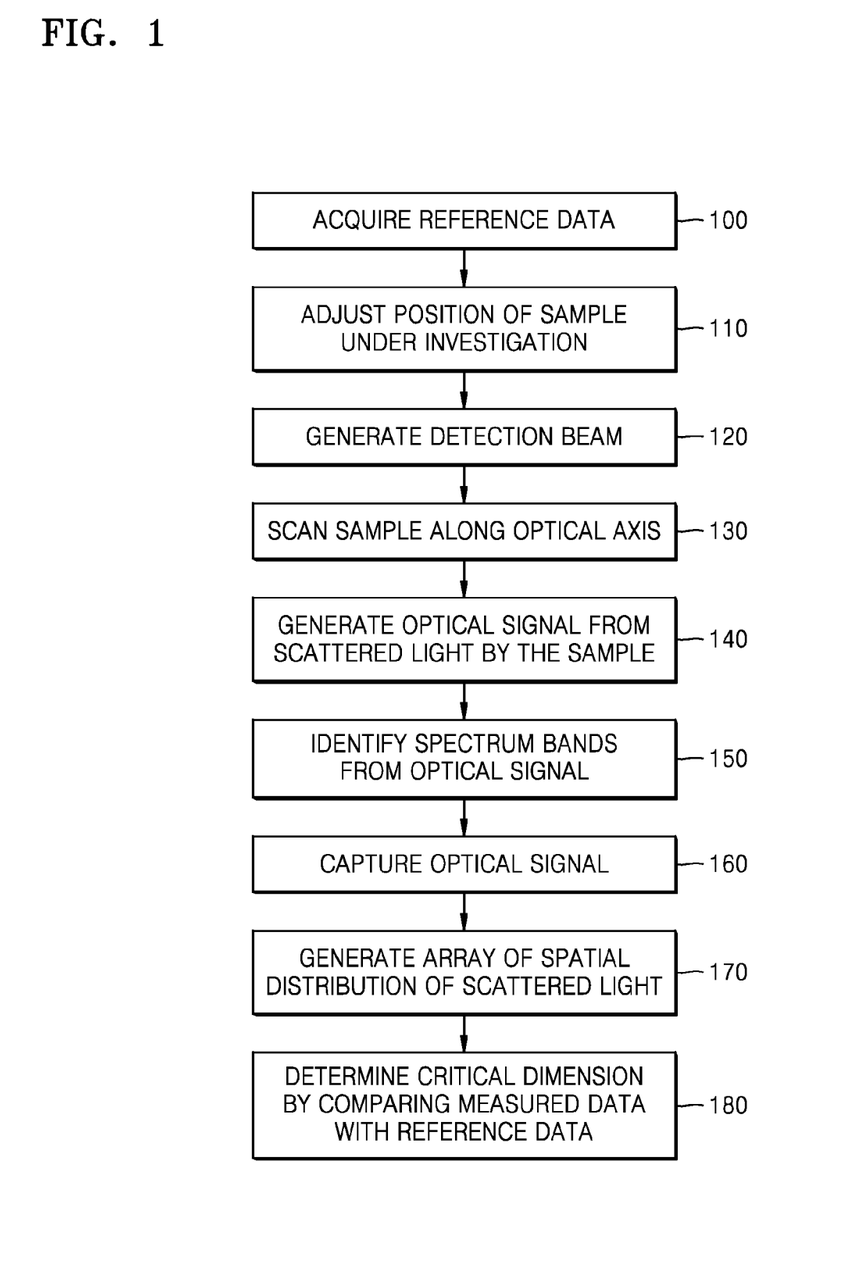
FIG. 1 shows a flowchart of a method of measuring a critical dimension of nanostructures, according to an exemplary embodiment.

FIG. 1 shows a flowchart of a method of measuring a critical dimension of nanostructures, according to an exemplary embodiment.

Referring to FIG. 1, reference data is acquired (S100). A library of reference arrays may be subsequently generated from the acquired reference data. Here, 'reference data' refers to values of scattered light intensity distribution acquired by illuminating reference objects or test objects with light having a broad frequency spectrum. The acquired reference data may then be represented as a library of reference arrays with a variables l, j, n, and m, where i is the horizontal resolution of an image sensor, j is the vertical resolution of the image sensor, n is the number of spectral bands (e.g. frequency bands) used, and m is the number of positions of a sample (i.e., a reference object or test object) along the optical axis.

Reference data may be acquired by measuring an intensity distribution of light scattered by calibrated reference objects. A reference object may be a standardized and calibrated object which is measured to obtain reference data (e.g., an amplitude and phase grating, a 3D arrays of rectangles, a single elongated rectangle, and a non-standard object having a complex shape with geometric parameters measured by electron microscopy). Furthermore, reference data (in particular, reference values of scattered light intensity distribution) may be obtained by mathematically modeling an intensity distribution of light scattered by reference objects having predetermined geometrical parameters. The mathematical modeling may be based on the solution of Maxwell's equations using numerical methods, such as a rigorous coupled wave analysis (RCWA) method or a finite difference time domain (FDTD) method.

Using a sample positioning device, a sample under investigation is positioned in an optical system that implements multispectral imaging for measuring a critical dimension of a nanostructure (110). The sample positioning device may be a device having any structure that is suitable for placing a sample in a desired position along an optical axis. To this end, the sample positioning device may include a linear three-axis motor-driven translator. In operation 110, a sample is placed in the optical system in the required position and is then illuminated with light having a broad frequency spectrum.

An optical radiation source. with a broad spectrum of radiated light generates a detection beam of light (120) The optical radiation source may be, for example, an illuminating optical system that illuminates a sample with light and contains an optical unit. The optical unit may include a light source 3, a set of lenses 4, 5, and 7, an amplitude mask 6, a beam splitter 8 and a micro lens 2, as shown, for example, in FIGS. 2 through 4.

The sample is scanned along the optical axis (130). A sample 1 may be moved by a sample positioning device such as a scanning device 12, as shown, for example, in FIGS. 2 through 4. To this end, the scanning device 12 may include a single-coordinate linear translator which may be, for example, as a piezoelectric nanopositioning system.

An optical signal is generated (140). The optical signal may be generated by projecting a detection beam through a set of lenses onto an object under investigation and focusing a beam scattered by the object under investigation onto a rear focal plane of the micro lens, thereby producing an image on the rear focal plane.

Figure 3:
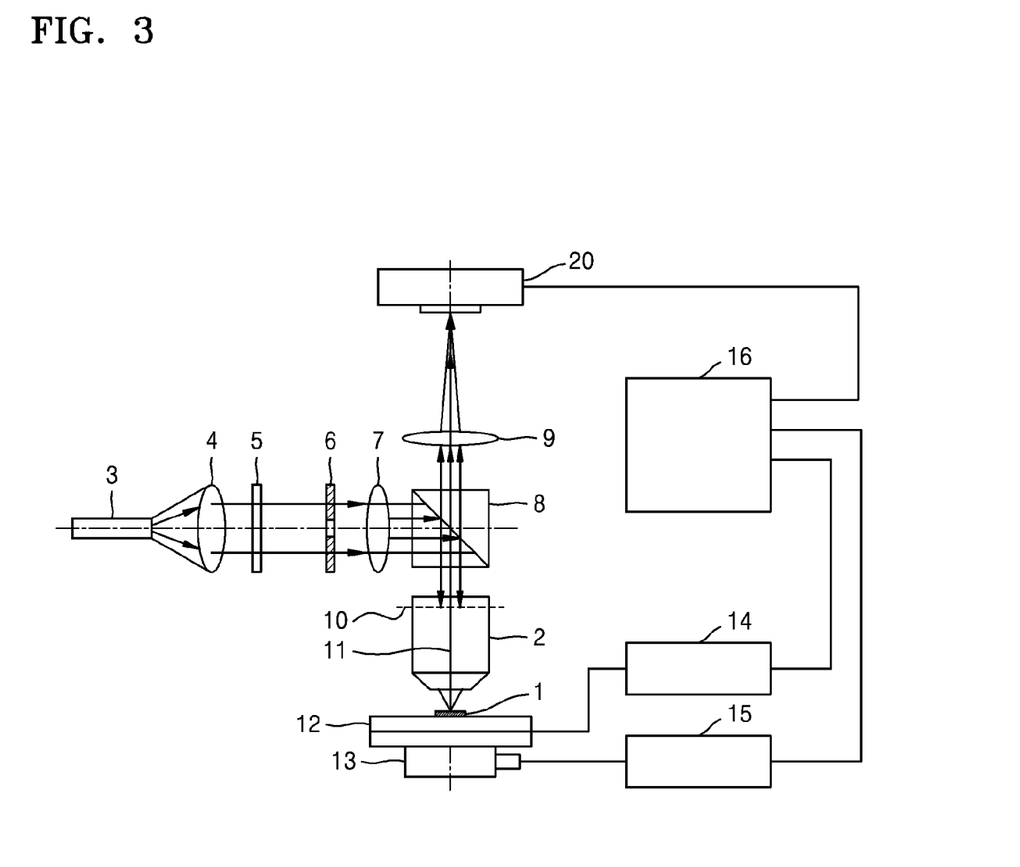
FIG. 3 is a schematic diagram of a device for measuring a critical dimension of nanostructures by implementing a method of multispectral imaging, according to another exemplary embodiment.
Figure 4:
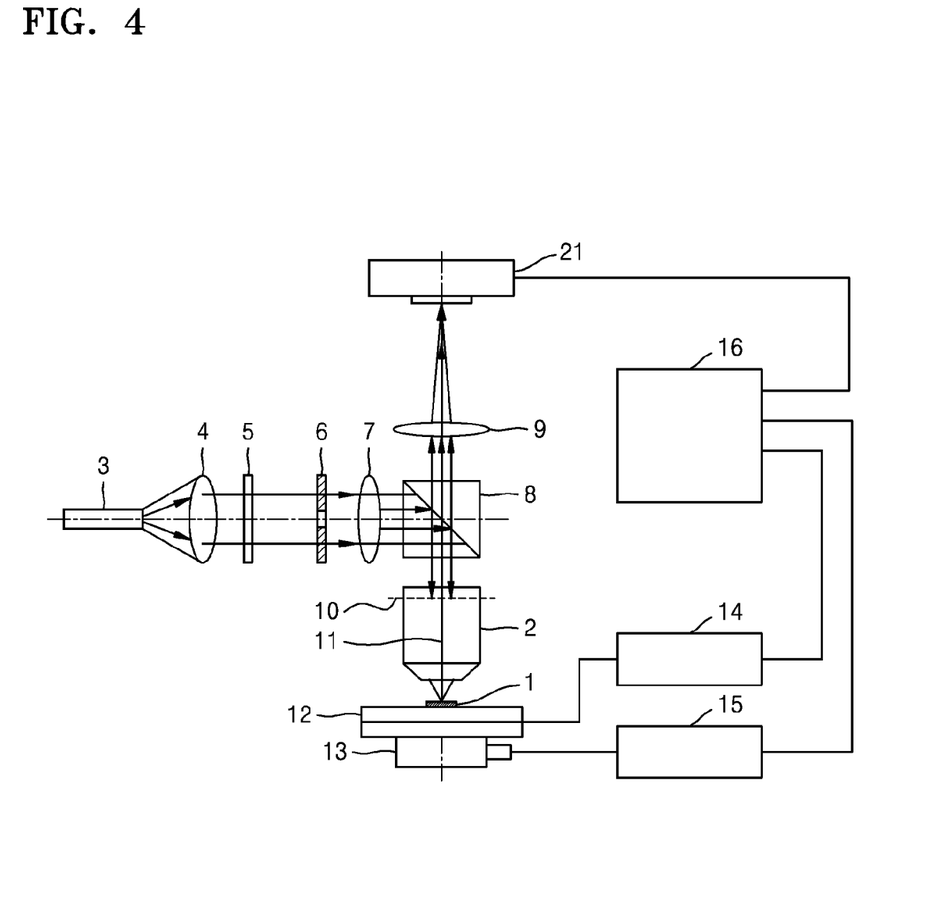
FIG. 4 is a schematic diagram of a device for measuring a critical dimension of nanostructures by implementing a method of multispectral imaging, according to another exemplary embodiment.

Spectral bands are identified in the optical signal generated in operation 140 (150). The spectral bands may be identified by varying a passband of a spectrum selection unit. To do this, a collecting optical system collects light scattered by the sample and transfers the collected light to the spectrum selection unit. The spectrum selection unit may include a set of colored filters 19 in a motor-driven frame, as shown in FIG. 2, an imaging spectrometer 20 including a monochromator and an appropriate optical system, as shown in FIG. 3, or a charge-coupled device (CCD) or complementary metal-oxide semiconductor (CMOS) array color image sensor 21, as shown in FIG. 4.

Figure 2:
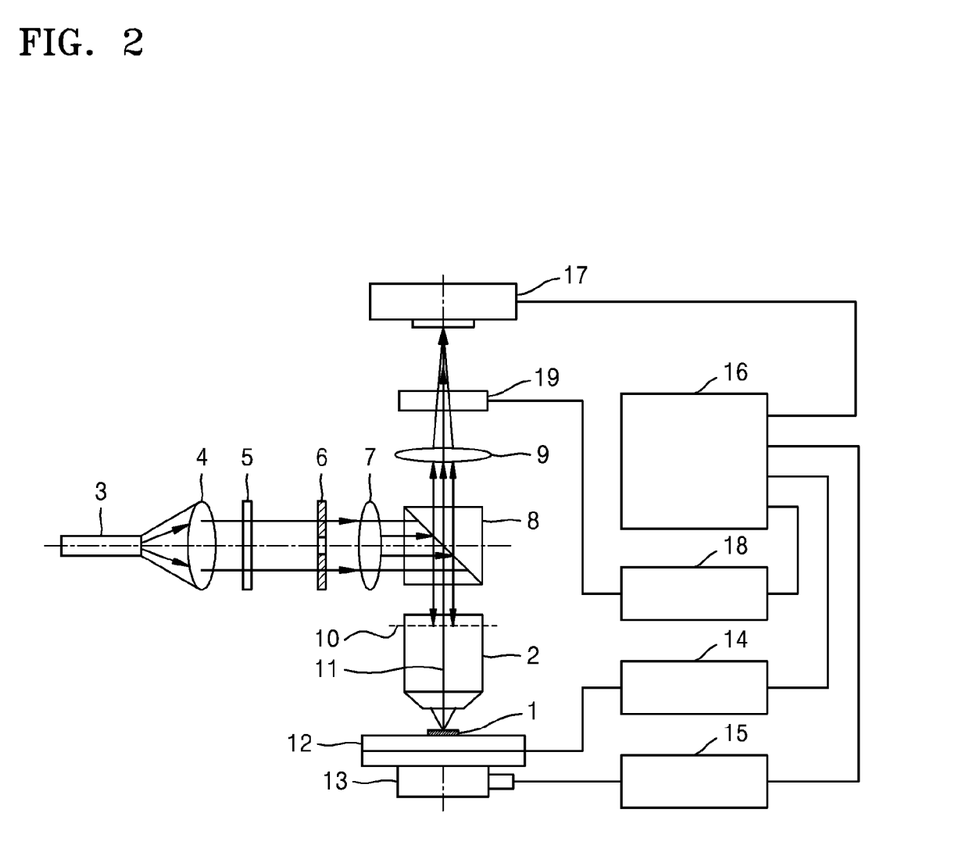
FIG. 2 is a schematic diagram of a device for measuring a critical dimension of nanostructures by implementing a method of multispectral imaging, according to another exemplary embodiment.

FIG. 2 is a schematic diagram of a device for measuring a critical dimension of nanostructures by implementing a method of multispectral imaging according to another exemplary embodiment, wherein the device may include a set of colored filters in a motor-driven frame. Also, FIG. 3 is a schematic diagram of a device for measuring a critical dimension of nanostructures by implementing a method of multispectral imaging according to another exemplary embodiment, wherein the device may include an imaging spectrometer. FIG. 4 is a schematic diagram of a device for measuring a critical dimension of nanostructures by implementing a method of multispectral imaging according to another exemplary embodiment, wherein the device may include an array color image sensor.

Referring to FIG. 1 the optical signal collected by the collecting optical system and processed by the spectral selection unit, corresponding to a plurality of sample positions along the optical axis and different spectral bands, is received (160). Reception (capture) of the optical signal is performed by an image sensor, for example, a CCD or CMOS array sensor 17, as shown in FIG. 2. A computing unit generates an array of spatial distribution of scattered light for different positions of the sample along the optical axis and different spectral bands based on the optical signal received by the image sensor (170) An intensity distribution array is formed for the investigated sample with a dimension i*j*m*n, where i is a horizontal resolution of the image sensor, j is a vertical resolution of the image sensor, n is the number of spectral bands used, and m is the number of positions of the sample (i.e., a reference object or a test object) along the optical axis.

The computing unit compares the measured data in the form of the array of spatial distribution of scattered light, generated in operation 170, with reference data in the form of reference arrays about a reference or test object, generated in operation 100 (180). From this comparison, the computing unit may acquire information about a critical dimension of the nanostructure (sample) under investigation.

Critical dimensions of a nanostructure may be determined in any of several ways. For example, a correlation coefficient between the positions of the samples along the optical axis and the scattered light intensity for analyzed wavelength ranges may be calculated for each of the measured data and the reference data, and then two correlation coefficients may be compared with each other to determine a critical dimension.

One or more of identification algorithms such as correlation coefficient, derivative difference module, Euclidean distance, distance module, or squared difference may be used to determine a critical dimension. The identification algorithm may be determined by comparing a spatial intensity distribution determined by the scattering of light by a structure under investigation with a corresponding reference spatial intensity distribution.

Since optical responses of various systems under different conditions are also different, a device for measuring a critical dimension may be preliminary trained before being used to determine a critical dimension of one or more objects.

FIG. 2 is a schematic diagram of a device for measuring a critical dimension of a nanostructure by implementing a method of multispectral imaging according to another exemplary embodiment. In FIG. 2, the device for measuring a critical dimension may adopt an optical microscopy scheme using the Koehler illumination method which operates in a bright field mode. The device for measuring the critical dimension of the nanostructure by implementing the method of multispectral imaging may include an optical radiation source which emits light with a broad spectrum; an illuminating optical system which illuminates a sample with light; a collecting optical system which collects light scattered by the sample; a spectrum selection unit; an image sensor; a sample positioning device; a controller; and a computing unit.

The optical radiation source may include a light source 3 (see FIGS. 2, 3, and 4). The illuminating optical system for illuminating a sample with light may be an optical assembly including a micro lens 2, a condenser lens 4, a polarizer 5, an amplitude mask 6, a beam splitter 8, and a transmitting lens 7 that projects an image of the amplitude mask 6 onto a rear focal plane 10 of the micro lens 2. These components are common to all exemplary embodiments presented herein.

The collecting optical system for collecting the light scattered by the sample may include the micro lens 2, including the rear focal plane 10 and a tube lens 9. The spectrum selection unit may include the set of colored filters 19 in the motor-driven frame, the imaging spectrometer 20, including a monochromator and an appropriate optical system, or the CCD or CMOS array color image sensor 21, depending on the embodiment. The image sensor for measuring a critical dimension of a nanostructure may be a CCD or CMOS array sensor 17. In some embodiments, the image sensor may be the imaging spectrometer 20 or a CCD or CMOS array color image sensor 21.

The sample positioning device may include a linear three-axis motor-driven translator 13 adapted to move the sample 1 under investigation into a desired position on the optical axis, for example, on the surface of an object stage, object table of microscope, or another similar support surface for placing a sample under investigation. To determine intensity distributions of light scattered at different positions of the sample 1, disposed in the sample positioning unit along the optical axis, the scanning device 12 may be used. The scanning device 12 may include a single-coordinate linear translator, for example, in the form of a piezoelectric nanopositioning system, or any other conventional system that adequately provides scanning to determine the intensity distribution of light scattered at different positions of the sample 1 under investigation.

The spectrum selection unit may include the set of colored filters 19, disposed in the motor-driven frame, between the tube lens 9 and the CCD or CMOS array sensor 17.

The controller may include controllers 14, 15, and 18 for controlling the scanning device 12, the sample positioning device (e.g. a linear three-axis motor-driven translator 13), and the spectrum selection unit. In the latter case, the controller 18 may control the set of colored filters 19 in the motor-driven frame.

The optical system of the device for measuring a critical dimension of a nanostructure by implementing a method of multispectral imaging may include the light source 3, the condenser lens 4, the polarizer 5, the amplitude mask 6, the beam splitter 8, the transmitting lens 7, and the tube lens 9, used for generating an image in a sensor plane, and the micro lens 2, including the rear focal plane 10 and an optical axis 11.

The light source 3 may provide illumination with a broad frequency band in order to generate an image of the sample 1. A light beam emitted from the light source 3 may pass through the condenser lens 4 and the polarizer 5. The polarizer 5 is rotatable by different angles to enable the desired light polarization to be selected.

The light may pass through the amplitude mask 6. The amplitude mask 6 may include an aperture of a predetermined shape and size to adjust the cross-sectional size and shape of the beam. The amplitude mask 6 may be disposed in a plane that is optically conjugated with the rear focal plane 10 of the micro lens 2.

Next, the light may pass through the transmitting lens 7. the transmitting lens 7 may be mounted between the amplitude mask 6 and the beam splitter 8. The light that passed through the transmitting lens 7 may be incident onto the beam splitter 8. The beam splitter 8 may split the light so that the light emitted from the light source 3 is incident onto the sample 1 under investigation that is placed on the linear three-axis motor-driven translator 13. The light reflected or scattered from the sample 1 under investigation may pass through the micro lens 2, the tube lens 9, and the spectrum selection unit to the image sensor. The beam splitter 8 may be any suitable beam splitter. For example, the beam splitter 8 may be a polarizing beam splitter.

The tube lens 9 may be a part of the collecting optical system. In this regard, the tube lens 9 may be mounted between the beam splitter 8 and the CCD or CMOS array sensor 17. The CCD or CMOS array sensor 17 may receive an optical signal generated by the spectrum selection unit and may convert the received optical signal into an electrical signal. The CCD or CMOS array sensor 17 may be an array image sensor. For example, the CCD or CMOS array sensor 17 may be a monochromatic CCD or CMOS array.

The sample 1 under investigation may be moved along the optical axis 11 by the scanning device 12. The computing unit 16 may include a computing device. The computing unit 16 may be a conventional computing device that is suitable for controlling an image captured by the CCD or CMOS array sensor 17 and managing the controllers 14, 15, and 18, as well as storing and processing the generated images. The computing unit 16 may be a general-purpose computer, a personal computer (PC), a processor, or the like. The computing unit 16 may include a single computer or a plurality of computers that are connected to each other via a network and capable of exchanging data and allocating functions among the computers in the network. The computing unit 16 may include appropriate software to perform the aforementioned functions for controlling as well as storing and processing images. The software may be embodied to suitably perform a method of measuring a critical dimension of a nanostructure. Also, the software may be embodied to suitably compare a reference array library including reference data with the acquired data. The software may be firmware, or one or more customized applications used to operate a system, but is not limited thereto. The software and also various types of data described above may be stored on computer-readable media and devices. The computer-readable media and devices may be volatile or nonvolatile storage devices, for example, a removable disk drive, hard disk, compact disc, digital versatile disc (DVD), random access memory (RAM), read only memory (ROM), or the like. The computer-readable media may be any electronic, magnetic, optical, electromagnetic, infrared, or semiconductor system or device, a semiconductor or solid-state memory, a magnetic tape, a hard magnetic disk and optical disk, a CD-ROM, a DVD, or the like.

FIG. 3 is a schematic diagram of a device for measuring a critical dimension of nanostructures by implementing a method of multispectral imaging, according to another exemplary embodiment. Descriptions of components of the device in FIG. 3, which are the same as those of the device in FIG. 2, will not be repeated. In contrast to the device of FIG. 2, the device of FIG. 3 may use an imaging spectrometer 20 as a spectrum selection unit and an image sensor. The imaging spectrometer 20 may include a monochromator, a predetermined optical system, and an image sensor. The device in FIG. 3 does not include the set of colored filters 19 in the motor-driven frame, as in the device of FIG. 2. The imaging spectrometer 20 in FIG. 3 may sequentially record an intensity distribution of light scattered by the sample 1 with respect to each of a plurality of spectral bands, but is not limited thereto.

FIG. 4 is a schematic diagram of a device for measuring a critical dimension of nanostructures by implementing a method of multispectral imaging, according to another exemplary embodiment. The device in FIG. 4 is similar to the devices described above, except that the spectrum selection unit and the image sensor include the CCD or CMOS array color image sensor 21. The CCD or CMOS array color image sensor 21 in FIG. 4 may concurrently record an intensity distribution of light scattered by the sample 1 with respect to each of a plurality of spectral bands, which are determined based on characteristics of a color image sensor.

As described in the aforementioned exemplary embodiments, different materials and technical methods may be used for selection of a spectrum and reception of an optical signal. In the exemplary embodiment of FIG. 2, for example, the set of colored filters 19 in a motor-driven frame may be used as a unit to split light which is reflected and scattered by the sample 1 and then passes through the micro lens 2, the beam splitter 8, and the tube lens 9 and reaches the CCD or CMOS array sensor 17. In the exemplary embodiment of FIG. 3, selection of spectrums and reception of optical signals may be performed in the imaging spectrometer 20. The imaging spectrometer 20 may include a means for selecting a spectrum (a monochromator or other means for representing spectrum regions of interest and obtaining images with wavelengths of interest) and an image sensor. In another exemplary embodiment, the selection of spectrums and the capture of images may be implemented by the CCD or CMOS array color image sensor 21. The array color image sensor 21 may include a CCD or CMOS array and allow the selection of spectrum regions of interest in color images by using appropriate software.

According to the exemplary embodiments described herein, a critical dimension of a nanostructure may be determined in a more efficient and accurate manner at a lower cost. In addition, the exemplary embodiments may be used in semiconductor production for checking geometric parameters of photomasks and elements of integrated circuits.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of measuring a critical dimension of a nanostructure, the method comprising:
    acquiring a reference intensity distribution, in each of a plurality of spectral bands, of light scattered by at least one reference object, for each of a plurality of positions of the at least one reference object disposed along an optical axis;
    generating, based on the reference intensity distributions, a library of reference intensity distribution arrays with a dimension i*j*m*n, wherein, i is a horizontal resolution of an image sensor, j is a vertical resolution of the image sensor, n is a number of the plurality of spectral bands, m is a number of the plurality of positions;
    positioning an object under investigation along the optical axis;
    illuminating the object under investigation with light in a broad frequency spectrum;
    collecting light scattered by the object under investigation and transmitting the light scattered by the object under investigation through a spectral selection unit and to an image sensor;
    the image sensor determining an intensity distribution, in each of the plurality of spectral ranges, of light scattered by the object under investigation, for each of a plurality of positions of the object under investigation, thereby determining a plurality of intensity distributions;
    generating, based on the plurality of determined intensity distributions, an intensity distribution array with a dimension i*j*m*n; and
    determining information about a critical dimension of the object under investigation by comparing the intensity distribution array with the library of reference intensity distribution arrays.

2. The method of claim 1, wherein
the light with the broad frequency spectrum is a range of wavelengths of about 380 nm to about 740 nm.

3. The method of claim 1, wherein
each of the at least one reference object is a calibrated reference object having known dimensions.

4. The method of claim 1, wherein
the generating the library of the reference intensity distribution arrays comprises mathematically modeling a reference intensity distribution of light scattered by each of the at least one reference object, wherein each of the at least one reference object has predetermined geometrical parameters.

5. The method of claim 4, wherein
the mathematically modeling comprises using a solution of Maxwell's equations using a numerical method.

6. The method of claim 5, wherein
the numerical method comprises at least one of a rigorous coupled wave analysis and a finite difference time domain method.

7. The method of claim 1, wherein
the transmitting the light scattered by the object under investigation through the spectral selection unit to the image sensor further comprises identifying spectral bands of the light collected by the spectrum selection unit.

8. A device for measuring a critical dimension of a nanostructure, the device comprising:
a light source which emits light in a broad frequency spectrum;
an illuminating optical system which transmits light emitted from the light source to a sample;
a collecting optical system which collects light scattered by the sample;
a spectrum selection unit which separates light collected by the collecting optical system into a plurality of spectral bands;
an image sensor on which light transmitted by the spectrum selection unit is incident;
a controller which generates an intensity distribution array with a dimension $i*j*m*n$, based on an intensity distribution of the light incident on the image sensor, wherein i is a horizontal resolution of the image sensor, j is a vertical resolution of the image sensor, n is the number of spectral bands, m is a number of positions of the sample disposed along an optical axis; and
a computing unit which determines a critical dimension of the sample based on the intensity distribution array.

9. The device of claim 8, further comprising:
the computing unit determines a critical dimension of a sample under investigation by comparing an intensity distribution array of the sample under investigation, generated by the controller, with an intensity distribution array of a reference sample, generated by the controller.

10. The device of claim 8, wherein
the light with the broad frequency spectrum is a range of wavelengths of about 380 nm to about 740 nm.

11. The device of claim 8, wherein
the illuminating optical system comprises a micro lens, a condenser lens, a polarizer, an amplitude mask, a beam splitter, and a transmitting lens which projects light transmitted by the amplitude mask onto the rear focal plane of the micro lens, thereby generating an image.

12. The device of claim 8, wherein
the spectrum selection unit comprises one of:
a plurality of colored filters disposed in a motor-driven frame, an imaging spectrometer comprising a monochromator, and a predetermined optical system,
a charge-coupled device; and
a complementary metal-oxide semiconductor array color image sensor.

13. The device of claim 8, wherein
the image sensor and the spectrum selection unit comprise an imaging spectrometer that sequentially records intensity distributions of light incident thereon, with respect to each spectral band.

14. The device of claim 8, wherein
the image sensor and the spectrum selection unit comprise one of:
a color image sensor based on a solid-state charge-coupled device; and
a complementary metal-oxide semiconductor array, and
the color image sensor concurrently records intensity distributions of light with respect to each spectral band.

15. A method of measuring a critical dimension of a test nanostructure, the method comprising:
obtaining, using a light source and an image sensor, a reference intensity distribution, in each of a plurality of spectral ranges, of light scattered by each of at least one reference nanostructure having known dimensions, for each of a plurality of positions of the at least one reference nanostructure disposed along an optical axis, thereby obtaining a plurality of reference intensity distributions;
generating, based on the plurality of reference intensity distributions, a library of reference intensity distribution arrays with a dimension $i*j*m*n$, wherein i is a horizontal resolution of the image sensor, n is a number of the plurality of spectral ranges, and m is a number of the plurality of positions;
positioning a test nanostructure in each of the plurality of positions;
at each of the plurality of positions, illuminating the test nanostructure with light in each of the plurality of spectral ranges;
collecting light scattered by the test nanostructure;
determining a test intensity distribution, in each of the plurality of spectral ranges, of the light scattered by the test nanostructure in each of the plurality of positions, thereby determining a plurality of test intensity distributions;
generating, based on the plurality of test intensity distributions, an intensity distribution array with a dimension $i*j*m*n$; and
determining at least one critical dimension of the test nanostructure based on a comparison of the library of intensity distribution arrays and the library of reference intensity distribution arrays and the known dimensions of the at least one reference nanostructure.

* * * * *